United States Patent
Dobrasko et al.

(10) Patent No.: US 7,390,777 B2
(45) Date of Patent: Jun. 24, 2008

(54) 1,2-DICHLOROETHYLENE COMPOSITIONS

(75) Inventors: Michael P. Dobrasko, Sulphur, LA (US); Ronald D. Olinger, Lake Charles, LA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 692 days.

(21) Appl. No.: 10/780,449

(22) Filed: Feb. 13, 2004

(65) Prior Publication Data
US 2006/0014661 A1 Jan. 19, 2006

(51) Int. Cl.
*C11D 7/50* (2006.01)
(52) U.S. Cl. .................................. 510/407; 510/365
(58) Field of Classification Search .............. 510/365, 510/407
See application file for complete search history.

(56) References Cited

U.S. PATENT DOCUMENTS

| | | | | |
|---|---|---|---|---|
| 3,455,835 A | 7/1969 | Burt | ............... | 252/172 |
| 3,496,241 A | 2/1970 | Berkowitz | ............... | 260/652.5 |
| 3,641,169 A | 2/1972 | Crabb et al. | ............... | 260/652.5 |
| 4,803,009 A | 2/1989 | Gorski | ............... | 252/171 |
| 4,804,493 A | 2/1989 | Gorski | ............... | 252/172 |
| 4,877,545 A | 10/1989 | Merchant et al. | ............... | 252/171 |
| 4,961,870 A | 10/1990 | Cook et al. | ............... | 252/171 |
| 4,971,085 A | 11/1990 | Magid et al. | ............... | 134/40 |
| 4,973,362 A | 11/1990 | Magid et al. | ............... | 134/42 |
| 5,064,560 A | 11/1991 | Merchant | ............... | 252/171 |
| 5,066,417 A | 11/1991 | Merchant | ............... | 252/171 |
| 5,116,525 A | 5/1992 | Merchant | ............... | 252/171 |
| 5,126,067 A | 6/1992 | Swan et al. | ............... | 252/171 |
| 5,851,977 A | 12/1998 | Gorton et al. | ............... | 510/412 |
| 5,902,412 A | 5/1999 | Taylor | ............... | 134/12 |
| 6,040,488 A | 3/2000 | Amato et al. | ............... | 570/264 |
| 6,100,229 A | 8/2000 | Swan et al. | ............... | 510/408 |
| 6,153,575 A | 11/2000 | Gorton et al. | ............... | 510/245 |

FOREIGN PATENT DOCUMENTS

| | | |
|---|---|---|
| EP | 1 319 649 A1 | 6/2003 |
| GB | 965858 | 6/1964 |
| JP | 09328444 | 12/1997 |

OTHER PUBLICATIONS

U.S. Appl. No. 10/436664; E.M. Gorton et al.; Method of Stabilizing Trichloroethane During Production; May 13, 2003.
U.S. Appl. No. 10/648972; E.M. Gorton et al.; Stabilized Trichloroethane; Aug. 27, 2003.
U.S. Appl. No. 10/648976; E. M. Gorton et al.; Method of Stabilizing Tetrachloroethylene During Production; Aug. 27, 2003.
U.S. Appl. No. 10/648970; E. M. Gorton et al.; Stabilized Polychloroethylenes; Aug. 27, 2003.

*Primary Examiner*—Gregory Webb
(74) *Attorney, Agent, or Firm*—Linda Pingitore; Irwin M. Stein

(57) ABSTRACT

Describes compositions of 1,2-dichloroethylene, particularly trans-1,2-dichloroethylene, stabilized with effective stabilizing amounts of a combination of (a) C3 to C12 alkylene oxide, e.g., butylene oxide, (b) alcohol chosen from aliphatic and cycloaliphatic alcohols having from 2 to 8 carbon atoms, e.g., isopropanol, and (c) a material chosen from (i) C1 to C5 alkoxyphenol, e.g., 4-methoxyphenol, (ii) free radical stabilizer having at least one 2,2,6,6-tetra(lower alkyl)-1-piperidinyloxy-yl group, and (iii) mixtures of (i) and (ii). Also describes use of such compositions for vapor degreasing of soiled articles, e.g., metal parts and soldered circuit boards.

23 Claims, No Drawings

1,2-DICHLOROETHYLENE COMPOSITIONS

The present invention relates to an organic solvent composition comprising 1,2-dichloroethylene. In particular, the present invention relates to a stabilized composition of 1,2-dichloroethylene, particularly trans 1,2-dichloroethylene. The present invention further relates to the use of such stabilized composition for cleaning the surface of articles, e.g., by vapor degreasing methods.

1,2-Dichloroethylene (CAS 540-59-0) is a chlorinated organic solvent that has been combined with a variety of other halocarbons, e.g., chlorocarbons (CC's), chlorofluorocarbons (CFC's), and hydrochlorofluorocarbons (HCFC's), to form azeotrope and azeotrope-like compositions for the purpose of cleaning the surface of articles. 1,2-dichloroethylene, particularly trans 1,2-dichloroethylene, improves the solvency property of the azeotrope and azeotrope-like compositions described above. These azeotrope and azeotrope-like compositions have found widespread use in industry for degreasing, e.g., vapor degreasing, and for otherwise cleaning of surfaces of various articles, e.g., metal parts, such as aluminum, aluminum alloys, copper, zinc, magnesium and iron parts, electric motors, compressors, delicate precision metal parts, and the flux and flux residues used in intricate shaped parts, such as printed circuit boards. Exposure of 1,2-dichloroethylene to such metals and to metal chlorides, which are frequently formed as a result of this exposure, has been observed to result in the degradation and/or decomposition of 1,2-dichloroethylene, which degradation/decomposition results in the formation of black tar-like substances. It is, therefore, necessary to incorporate one or more additives with the 1,2-dichloroethylene to stabilize it against degradation/decomposition during degreasing applications, particularly vapor degreasing applications.

In its simplest form, vapor degreasing or solvent cleaning comprises a method in which the article to be cleaned, which is generally at room temperature, is exposed to the vapors of a boiling solvent. Vapors condensing on the article provide clean distilled solvent to wash away grease, contaminating amounts of metals, such as iron, copper, aluminum and zinc, or other contamination. Final evaporation of the solvent from the article leaves behind no residue, as would be the case where the article is simple washed in liquid solvent.

For difficult to remove soils, where elevated temperatures are necessary to improve the cleaning action of the solvent, or for large volume assembly line operations where the cleaning of metal parts and assemblies must be done efficiently and quickly, the conventional operation of a vapor degreaser comprises immersing the article to be cleaned in a sump of boiling solvent, which removes the bulk of the contaminating soil, thereafter immersing the article in a sump containing freshly distilled solvent near room temperature, and finally exposing the article to solvent vapors over the boiling sump, which vapors condense on the cleaned article and remove any remaining soil. Vapor degreasers are well known in the art. See, for example, U.S. Pat. No. 3,085,918, which discloses vapor degreasers comprising a boiling sump, a clean sump, a water separator and other ancillary equipment.

1,2-Dichloroethylene exists as two geometric isomers: namely, trans 1,2-dichloroethylene (CAS 156-60-5) and cis 1,2-dichloroethylene (CAS 156-59-2). The isomers of 1,2-dichloroethylene have distinct chemical and physical properties. In particular, the trans-isomer has a lower boiling point, density, viscosity and surface tension than the cis-isomer. However, the trans isomer is flammable. A drawback of the cis isomer is that it can form chloroacetylene if it comes into contact with caustic, e.g., sodium hydroxide. Chloroacetylene can be explosive, and hence use of the cis isomer in cleaning applications where caustic is also used is not desirable. At equilibrium, 1,2-dichloroethylene typically exists as a mixture of the two isomers in a 4:1 weight ratio of cis:trans.

For cleaning applications that require a low residue producing solvent, such as in the cleaning of mechanical components of high quality and precision, the trans-isomer is the more desired isomer. Accordingly, it would be desirable to provide a stabilized 1,2-dichloroethylene that is predominantly the trans-isomer, e.g., at least 99.5 weight percent trans.

It has now been discovered that 1,2-dichloroethylene, particularly trans-1,2-dichloroethylene, can be stabilized against decomposition/degradation and that this stabilized composition can be used to degrease articles, e.g., by vapor degreasing methods. In accordance with the present invention, there are provided stabilized liquid 1,2-dichloroethylene compositions, e.g., trans-1,2-dichloroethylene compositions, comprising 1,2-dichloroethylene as the predominant halohydrocarbon in the composition and effective stabilizing amounts of each of:

(a) alkylene oxide having from 3 to 12 carbon atoms and a vicinal epoxy group, (b) alcohol chosen from aliphatic and cycloaliphatic alcohols having from 2 to 8 carbon atoms, and (c) a material chosen from (i) lower alkoxyphenol, (ii) a free radical stabilizer having at least one 2,2,6,6-tetra(lower alkyl)-1-piperidinyloxy-yl group or 2,2,5,5-tetra(lower alkyl) pyrrolidinyloxy group and (iii) mixtures of said lower alkoxyphenol and free radical stabilizer.

DETAILED DESCRIPTION OF THE INVENTION

For purposes of this specification (other than in the operating examples), unless otherwise indicated, all numbers expressing quantities and ranges of ingredients are to be understood as modified in all instances by the term "about". Accordingly, unless indicated to the contrary, the numerical parameters set forth in this specification and attached claims are approximations that can vary depending upon the desired object sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Further, as used in this specification and the appended claims, the singular forms "a", "an" and "the" are intended to include plural referents, unless expressly and unequivocally limited to one referent.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is having a minimum value equal to or grater than 1 and a maximum value of equal to or less than 10. Because the disclosed numerical ranges are continuous, they include every value between the minimum and maximum values. Unless expressly indicated otherwise, the various numerical ranges specified in this application are approximations.

The specific citation in this specification of patent applications, published or granted patents and published articles, such as the disclosures in identified patents that are referred to by column and line number, are incorporated herein, in toto, by reference.

In an embodiment of the present invention, 1,2-dichloroethylene is the primary solvent-providing halohydrocarbon of the solvent compositions, e.g., the 1,2-dichloroethylene, particularly trans 1,2-dichloroethylene, is present in major amounts in the solvent composition. In particular, the 1,2-dichloroethylene is present in the solvent composition in amounts of at least 80 weight percent, desirably at least 90 weight percent, more desirably at least 99 weight percent, and still more desirably at least 99.5 weight percent, based on the total weight of the halohydrocarbons in the solvent composition and excluding the stabilizer components. The solvent composition of the present invention is typically non-azeotropic, but where other halohydrocarbons are present in more than incidental amounts, it is possible to form azeotrope or azeotrope-like compositions. As is recognized in the art, it is not possible to predict what compositions will form an azeotrope or azeotrope-like mixture.

Similarly, liquid 1,2-dichloroethylene compositions comprising trans-1,2-dichloroethylene as the predominant 1,2-dichloroethylene can contain minor amounts of the cis-isomer, such as less than 20 weight percent, more particularly less than 10 or 5 weight percent, still more particularly less than 3, 1, or 0.5 weight percent. The amount of the cis isomer in the trans-1,2-dichloroethylene can vary accordingly from 0.15 to 20, generally from 0.15 to 10, more generally from 0.3 to 5, still more generally from 0.5 to 1 or 3 weight percent, the presence of which is considered not to detract from the efficacy of trans-1,2-dichloroethylene as a degreasing solvent. The level of the cis-isomer in trans-1,2-dichloroethylene can vary between any of the stated values, including the recited values.

Alkylene oxides having from 3-12 carbon atoms and having a vicinal epoxy group that can be used as a stabilizer in the 1,2-dichloroethylene composition can be represented by the general formula,

wherein R and R1 are divalent aliphatic or alicyclic radicals that can be substituted with an aliphatic, alicyclic or aromatic group and that can have on the aliphatic or alicyclic radical (or a substituent thereon) one or more epoxy, hydroxy or alkoxy groups. Non-limiting examples of such alkylene oxides include glycidol, propylene oxide, 1,2-epoxy butane (butylene oxide), 2,3-butylene oxide, cis-2,3-pentene oxide, 2-methyl-2,3-epoxybutane, 1,2-epoxy cyclopentene, 2,3-dimethyl-2,3-epoxybutane, 2-chloro-3,4-epoxybutane, 1-chloro-2,3-epoxybutane, and 1,2-epoxycyclohexane.

Alcohols that can be used as a stabilizer in 1,2-dichloroethylene compositions are those having 2 to 8 carbon atoms and one or more hydroxyl groups. Typically, the alcohol is free of non-hydroxyl substituents having other than carbon and hydrogen atoms. Non-limiting examples of such alcohols include ethanol, 1-propanol, 2-propanol (isopropyl alcohol), 1-butanol, 2-butanol, 2-methyl-2-propanol, 2-methyl-1-propanol, 1-pentanol, 2-pentanol, 3-pentanol, 2-methyl-1-butanol, 2,2-dimethyl-1-propanol, 3-ethyl-3-pentanol, cyclohexyl alcohol and the like.

Lower alkoxyphenols that can be used as a stabilizer in 1,2-dichloroethylene compositions are those having from 1 to 5 carbon atoms, e.g., 1 to 2 carbon atoms, in the alkoxy group. Non-limiting examples of such alkoxyphenols include methoxyphenol, ethoxyphenol, propoxyphenol, n-butoxyphenol, and amyloxyphenol. In particular, the 4-alkoxyphenols, such as 4-methoxyphenol (hydroquinone monomethyl ether) are desired.

An example of stable free radical stabilizer material that can be used as a stabilizer in 1,2-dichloroethylene compositions, e.g., trans 1,2-dichloroethylene solvent compositions, is a material that has at least one 2,2,6,6-tetra (lower alkyl)-1-piperidinyloxy-yl free radical group. The lower alkyl groups can be the same or they can be different, but usually they will be the same, and will comprise from 1 to 5, e.g., 1 to 4, carbon atoms. The lower alkyl group usually employed is methyl or ethyl, although lower alkyl groups having more than two carbon atoms, e.g., three or four carbon atoms, are contemplated. Typically, the lower alkyl group is methyl.

The 2,2,6,6-tetra(lower alkyl)-1-piperidinyloxy-yl free radical group is usually the 2,2,6,6-tetra(lower alkyl)-1-piperidinyloxy-4-yl free radical group, but the 2,2,6,6-tetra (lower alkyl)-1-piperidinyloxy-3-yl free radical group can be used if desired. The 2,2,6,6-tetra(lower alkyl)-1-piperidinyloxy-yl free radical group can be attached to other moieties, e.g., hydrogen, hydroxyl, oxo, or to a parent compound as a substituent. In those embodiments in which the stable free radical is substituted onto a parent compound, the typical parent compound is a monocarboxylic acid or a dicarboxylic acid, in which case the stable free radical stabilizer material is an ester. The monocarboxylic acids can be aliphatic or aromatic. In one contemplated embodiment, the aliphatic monocarboxylic acid is saturated and contains from 1 to 18 carbon atoms. In other contemplated embodiments, the aliphatic monocarboxylic acid contains from 2 to 12 carbon atoms, e.g., from 3 to 8 carbon atoms. Of the aromatic monocarboxylic acids, benzoic acid is a particular desired embodiment. When dicarboxylic acids are used as the parent compound, the dicarboxylic acids can be saturated and contain from 2 to 13 carbon atoms. In one contemplated embodiment, the saturated dicarboxylic acid contains from 4 to 12 carbon atoms, e.g., from 8 to 12 carbon atoms. A particular contemplated embodiment of a saturated dicarboxylic acid is sebacic acid, which contains 10 carbon atoms. It should be understood that the stable free radical material of the present invention need not be associated with a parent compound, and in embodiments of the present invention, the stable free radical material itself is used.

Stable free radicals described herein and methods for their preparation are known to those skilled in the art. Non-limiting examples of suitable 2,2,6,6-tetra(lower alkyl)-1-piperidinyloxy-yl free radical materials that can be used to stabilize trans 1,2-dichloroethylene compositions of the present invention include:

2,2,6,6-tetramethyl-1-piperidinyloxy [CAS 2564-83-2];

2,2,6,6-tetramethyl-4-hydroxy-1-piperidinyloxy [CAS 2226-96-2]

having the structure:

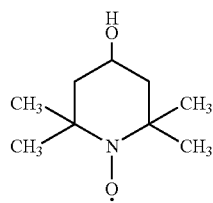

which material is also known as 4-hydroxy-TEMPO, and which is commercially available as a 5% active ingredient in an inert solvent mix from GE Betz as PETROFLO 20Y104, and which is also available in solid form from Ciba Specialty Chemicals as PROSTAB 5198;

2,2,6,6-tetramethyl-4-oxo-1-piperidinyloxy [CAS 2896-70-0];
2,2,6,6-tetramethyl-4-amino-piperidinyloxy;
2,2,6,6-tetramethyl-4-dimethylamino-piperidinyloxy;
2,2,6,6-tetramethyl-4-ethanoyloxy piperidinyloxy;
2,2,6,6-tetramethyl-4-((methylsulfonyl)oxy)-1-piperidinyloxy [CAS 35203-66-8];
2,2,6,6-tetramethyl-1-piperidinyloxy-4-yl benzoate [CAS 3225-26-1]; and
bis(2,2,6,6-tetramethyl-1-piperidinyloxy-4-yl) sebacate [CAS 2516-92-9], which is available commercially in solid form, and as a 4 to 10% solution in an organic solvent from Ciba Specialty Chemicals as PROSTAB 5415.

Other examples of free radical stabilizer materials that are contemplated for stabilizing the 1,2-dichloroethylene compositions, e.g., trans 1,2-dichloroethylene compositions, described herein include materials having a 2,2,5,5-tetra (lower alkyl) pyrrolidinyloxy group. As in the case of the 2,2,6,6-tetra(lower alkyl)-1-piperidinyloxy-yl group described heretofore, the lower alkyl groups can be the same or different, but usually will be the same, and will comprise from 1 to 5, e.g., 1 to 4, carbon atoms. The lower alkyl group usually employed is methyl or ethyl. Typically, the lower alkyl group is methyl, e.g., 2,2,5,5-tetramethyl pyrrolidinyloxy. Non-limiting examples of such stabilizer materials include:

2,2,5,5-tetramethyl-pyrrolidinyloxy;
3-amino-2,2,5,5-tetramethyl-pyrrolidinyloxy;
2,2,5,5-tetramethyl-1-oxa-3-azacyclopentyl-3-oxy; and
2,2,5,5-tetramethyl-3-pyrrolinyl-1-oxy-3-carboxylic acid.

By "effective stabilizing amount" of the stabilizing components is meant that the amount of each stabilizer component, which when combined with the amounts of the other stabilizing components in the 1,2-dichloroethylene, e.g., trans-1,2-dichloroethylene, solvent composition allows the 1,2-dichloroethylene to be stored and used commercially as a cleaning solvent, e.g., a vapor degreasing solvent. Each of the stabilizer components described herein and their methods of preparation are known to those skilled in the art. The stabilizer components described herein are generally commercially available, and if not commercially available can be prepared by methods known in the art.

Typically, from 0.1 to 0.4 weight percent, more typically from 0.2 to 0.3 weight percent, of alkylene oxide, e.g., 1,2-butylene oxide, based on the weight of 1,2-dichloroethylene in the composition, can be used.

Generally, from 0.2 to 0.8 weight percent, more generally from 0.45 to 0.65 weight percent, of the alcohol stabilizer, based on the weight of 1,2-dichloroethylene in the composition, can be used.

In one embodiment of the present invention, the lower alkoxyphenol stabilizer is not used. In another embodiment of the present invention, it is used in combination with the alkylene oxide and alcohol stabilizers, and optionally with the free-radical stabilizer. When it is used, the alkoxyphenol stabilizer is used typically in amounts of from 0.002 to 0.02 weight percent, more typically from 0.0085 to 0.0115 weight percent, based on the weight of 1,2-dichloroethylene in the composition.

In a further embodiment of the present invention, the material comprising the free-radical stabilizer is not used. In a still further embodiment of the present invention, it is used in combination with the alkylene oxide and alcohol stabilizers, and optionally with the lower alkoxyphenol stabilizer. When it is used, the material comprising the free-radical stabilizer is used generally in amounts of from 0.001 to 0.0075 weight percent, more generally from 0.0025 to 0.005 weight percent, based on the weight of 1,2-dichloroethylene in the composition. At least one of the lower alkoxyphenol stabilizer and the material comprising the free-radical stabilizer is used to stabilize the 1,2-dichloroethylene solvent composition (in combination with the alkylene oxide and alcohol stabilizers), and in a particular embodiment of the present invention, both the lower alkoxyphenol stabilizer and material comprising the free-radical stabilizer are so used.

The amount of each of the stabilizer components described above can vary between any combination of their recited values, inclusive of the recited values. The numerical amounts of the stabilizer components stated herein are the amounts that are generally considered to be effective stabilizing amounts; however, use of more or less of the stabilizer components can be effective in specific instances and is an embodiment within the scope of the present invention. Generally, higher amounts offer no particular advantages under normal vapor degreasing conditions, and are therefore economically not attractive.

The compositions of the present invention can be prepared by any convenient method including weighing a desired quantity of each of the components comprising the composition components into a mixing vessel, and thereafter mixing them in any known manner.

The present invention is more particularly described in the following examples, which are intended as illustrative only, since numerous modifications and variations therein will be apparent to those skilled in the art.

EXAMPLES 1-8

In each of the following examples, 50 milliliters (ml) of commercial trans-1,2-dichloroethylene (PPG Industries, Inc.) containing the indicated stabilizers in the amounts specified in Table 1 is refluxed in a 125 ml Erlenmeyer flask equipped with a water-cooled condenser in the presence of 1 gram each of turnings of the aluminum alloys 2024 and 7075, and 0.5 grams of reagent grade anhydrous aluminum chloride for up to 24 hours. If the test solvent remains clear and colorless to slightly colored with no appreciable tar formation after the test period, the solvent is considered to have passed. Conversely, if the test solvent turns opaque and dark brown to black in color anytime within the 24-hour test period of reflux, the solvent is considered to have failed, e.g., decomposed/degraded. Tar formation is associated with a failing test.

In the following examples, the stabilizers used were butylene oxide (BO), isopropyl alcohol (IPA), 4-hydroxy TEMPO (TEMPO), and 4-methoxyphenol (HQMME). The trans-1,2-dichloroethylene contained 0.026 weight percent of the cis isomer, and various amounts of residual water from the manufacturing process, as indicated in Table 1. In Table 1, all specified amounts of water and stabilizer are reported as parts per million (ppm).

TABLE 1

| | STABILIZER, ppm | | | | | |
|---|---|---|---|---|---|---|
| EXAMPLE/ | WATER | BO | IPA | TEMPO | HQMME | PASS/FAIL |
| 1 | 105 | 3214 | 3883 | 25 | 20 | PASSa |
| 2 | 110 | 2494 | 1991 | 26 | — | PASSb |
| 3 | 28 | 1150 | 3300 | 31 | — | PASSc |
| 4 | 30 | 2500 | 3400 | 32 | 89 | PASSd |
| 5 | 45 | 2000 | 5000 | 15 | — | PASSe |
| 6 | 45 | 2000 | 5000 | — | 100 | PASSf |
| 7 | 23 | 1005 | — | — | 90 | FAILg |
| 8 | 25 | 2119 | — | — | 90 | FAILh | aAfter 24 hours reflux, solvent is clear and pale yellow in color with very little tar.
bAfter 24 hours reflux, solvent is clear and charcoal gray in color with very little tar.
cAfter 24 hours reflux, solvent is clear and colorless with only a few black particles present.
dAfter 24 hours reflux, solvent is clear and light tan in color with only a few black particles present.
eAfter 24 hours reflux, solvent is clear and light yellow in color with only a few black particles present.
fAfter 24 hours reflux, solvent is clear and light gray in color with only a few black particles present.
gAfter 2 hours reflux, solvent is dark brown in color with considerable tar observed.
hAfter 2 hours reflux, solvent is dark brown in color with considerable tar observed.

The data of Table 1 demonstrates that the combination of an alkylene oxide, e.g., butylene oxide, aliphatic alcohol, e.g., isopropyl alcohol, and lower alkoxyphenol, e.g., 4-methoxyphenol, and/or free radical stabilizer, e.g., 4-hydroxy TEMPO, stabilizes trans 1,2-dichloroethylene in the aluminum/aluminum chloride reflux test, which indicates that such stabilized 1,2-dichloroethylene is useful in the vapor degreasing of metal articles.

The present invention has been described with reference to specific details of particular embodiments thereof. It is not intended that such details be regarded as limitations upon the scope of the invention except insofar as and to the extent that they are included in the accompanying claims.

What is claimed is:

1. A non-azeotropic solvent composition consisting essentially of trans 1,2-dichloroethylene and an effective stabilizing amount of each of:
   a. alkylene oxide having from 3 to 12 carbon atoms and a vicinal epoxy group,
   b. alcohol chosen from aliphatic and cycloaliphatic alcohols having from 2 to 8 carbon atoms, and
   c. material chosen from (i) lower alkoxyphenol, (ii) free radical stabilizer having at least one 2,2,6,6-tetra(lower alkyl)-1-piperidinyloxy-yl group or 2,2,5,5-tetra(lower alkyl)pyrrolidinyloxy group, or (iii) mixtures of (i) and (ii), wherein the trans 1,2-dichloroethylene is the primary solvent-providing halohydrocarbon of the solvent composition.

2. A composition according to claim 1 wherein the alkylene oxide has from 3 to 4 carbon atoms.

3. A composition according to claim 2 wherein the alkylene oxide is butylene oxide.

4. A composition according to claim 1 wherein the alcohol is an aliphatic alcohol having from 3 to 4 carbon atoms.

5. A composition according to claim 1 wherein the lower alkoxyphenol is a 4-alkoxyphenol.

6. A composition according to claim 5 wherein the 4-alkoxyphenol is 4-methoxyphenol.

7. A composition consisting essentially of trans 1,2-dichloroethylene and an effective stabilizing amount of each of:
   a. butylene oxide,
   b. isopropyl alcohol, and
   c. a free radical stabilizer material having at least one 2,2,6,6-tetra(lower alkyl)-1-piperidinyloxy-yl free radical group.

8. The composition of claim 7 further containing an effective stabilizing amount of 4-methoxyphenol.

9. A composition consisting essentially of trans 1,2-dichloroethylene and an effective stabilizing amount of each of:
   a. butylene oxide,
   b. isopropyl alcohol, and
   c. 4-methoxyphenol.

10. A liquid non-azeotropic halohydrocarbon vapor degreasing solvent composition comprising 1,2-dichloroethylene as the primary halohydrocarbon degreasing solvent and an effective stabilizing amount of each of:
    a. alkylene oxide having from 3 to 12 carbon atoms and a vicinal epoxy group,
    b. alcohol chosen from aliphatic and cycloaliphatic alcohols having from 2 to 8 carbon atoms, and
    c. material chosen from (i) lower alkoxyphenol, (ii) free radical stabilizer having at least one 2,2,6,6-tetra(lower alkyl)-1-piperidinyloxy-yl group or 2,2,5,5-tetra(lower alkyl)pyrrolidinyloxy group, or (iii) mixtures of (i) and (ii).

11. The liquid composition of claim 10 wherein the 1,2-dichloroethylene is principally trans-1,2-dichloroethylene.

12. A composition consisting essentially of trans 1,2-dichloroethylene and an effective stabilizing amount of each of:
    a. alkylene oxide having from 3 to 12 carbon atoms and a vicinal epoxy group,
    b. isopropanol, and
    c. material chosen from (i) lower alkoxyphenol, (ii) free radical stabilizer having at least one 2,2,6,6-tetra(lower alkyl)-1-piperidinyloxy-yl group or 2,2,5,5-tetra(lower alkyl)pyrrolidinyloxy group, or (iii) mixtures of (i) and (ii).

13. A composition consisting essentially of trans 1,2-dichloroethylene and an effective stabilizing amount of each of:
    a. alkylene oxide having from 3 to 12 carbon atoms and a vicinal epoxy group,
    b. alcohol chosen from aliphatic and cycloaliphatic alcohols having from 2 to 8 carbon atoms, and
    c. material chosen from free radical stabilizer having at least one 2,2,6,6-tetra(methyl)-1-piperidinyloxy-yl group.

14. A composition consisting essentially of trans 1,2-dichloroethylene and an effective stabilizing amount of each of:
    a. alkylene oxide having from 3 to 12 carbon atoms and a vicinal epoxy group,
    b. alcohol chosen from aliphatic and cycloaliphatic alcohols having from 2 to 8 carbon atoms, and
    c. material chosen from free radical stabilizer having at least one 2,2,5,5-tetra(lower alkyl)pyrrolidinyloxy group.

15. A liquid halohydrocarbon vapor degreasing solvent composition comprising 1,2-dichloroethylene as the primary degreasing solvent and an effective stabilizing amount of each of:
    a. butylene oxide, b. isopropanol, and c. material chosen from (i) 4-methoxyphenol, (ii) free radical stabilizer having at least one 2,2,6,6-tetra(methyl)-4-hydroxy-1-piperidinyloxy, or (iii) mixtures of (i) and (ii), wherein the 1,2-dichloroethylene is principally trans-1,2-dichloroethylene.

16. A composition according to claim 13 wherein the free radical stabilizer is a material having a 2,2,6,6-tetra(methyl)-1-piperidinyloxy-4-yl group.

17. A composition according to claim 16 wherein to free radical stabilizer is a material having the free radical group: 2,2,6,6-tetramethyl-4-hydroxy-1-piperidinyloxy, 2,2,6,6-tetramethyl-4-amino-piperidinyloxy, 2,2,6,6-tetramethyl-4-dimethylamino-piperidinyloxy, 2,2,6,6-tetramethyl-4-ethanoyloxy piperidinyloxy, 2,2,6,6-tetramethyl-4-oxo-1-piperidinyloxy or 2,2,6,6-tetramethyl-4-{(methylsulfonyl)oxy}-1-piperidinyloxy.

18. A composition according to claim 16 wherein the free radical stabilizer is a material having the 2,2,6,6-tetramethyl-1-piperidinyloxy-4-yl benzoate free radical group.

19. A composition according to claim 16 wherein the free radical stabilizer is a bis(2,2,6,6-tetramethyl-1-piperidinyloxy-4-yl) ester of a saturated dicarboxylic acid.

20. A composition according to claim 19 wherein the saturated dicarboxylic acid contains from 2 to 13 carbon atoms.

21. A composition according to claim 20 wherein the free radical stabilizer is bis(2,2,6,6-tetramethyl-1-piperidinyloxy-4-yl) sebacate.

22. A composition according to claim 14 wherein the 2,2,5,5-tetra(lower alkyl)pyrrolidinyloxy group is 2,2,5,5-tetramethyl pyrrolidinyloxy.

23. A composition according to claim 14 wherein the free radical stabilizer is a material having a 2,2,5,5-tetramethyl-3-amino-pyrrolidinyloxy, 2,2,5,5-tetramethyl-1-oxa-3-azacyclopentyl-3-oxy, or 2,2,5,5-tetramethyl-3-pyrrolinyl-1-oxy-3carboxylic acid group.

* * * * *